US008693613B2

(12) United States Patent
Bueno et al.

(10) Patent No.: US 8,693,613 B2
(45) Date of Patent: Apr. 8, 2014

(54) NUCLEAR FUEL PELLET INSPECTION (75) Inventors: Clifford Bueno, Clifton Park, NY (US); Patrick Kenneth Hogan, Hampstead, NC (US); Mark John Osterlitz, Schenectady, NY (US); William Robert Ross, Rotterdam, NY (US)

(73) Assignee: General Electric Company, Niskayuna, NY (US)

( * ) Notice: Subject to any disclaimer, the term of this patent is extended or adjusted under 35 U.S.C. 154(b) by 1364 days.

(21) Appl. No.: 12/687,704

(22) Filed: Jan. 14, 2010

(65) Prior Publication Data

US 2011/0170654 A1 Jul. 14, 2011

(51) Int. Cl.
*G21C 3/40* (2006.01)

(52) U.S. Cl.
USPC ........................................................ 376/450

(58) Field of Classification Search
USPC ........................................................ 376/450
See application file for complete search history.

(56) References Cited

U.S. PATENT DOCUMENTS

| | | | |
|---|---|---|---|
| 4,994,232 A * | 2/1991 | Brashier et al. | 376/261 |
| 5,108,959 A | 4/1992 | Buchanan et al. | |
| 5,120,970 A | 6/1992 | Buchanan et al. | |
| 5,122,671 A | 6/1992 | Buchanan et al. | |
| 5,391,320 A | 2/1995 | Buchanan et al. | |
| 5,594,253 A | 1/1997 | Bueno et al. | |
| 5,602,646 A | 2/1997 | Bernardin et al. | |
| 5,606,410 A | 2/1997 | Peclier et al. | |
| 5,636,299 A | 6/1997 | Bueno et al. | |
| 6,018,563 A | 1/2000 | Arai et al. | |
| 6,442,237 B1 | 8/2002 | Corby, Jr. et al. | |
| 6,466,643 B1 | 10/2002 | Bueno et al. | |
| 6,614,872 B2 | 9/2003 | Bueno et al. | |
| 6,618,465 B2 | 9/2003 | Mohr et al. | |
| 6,662,088 B1 | 12/2003 | Hopple et al. | |
| 7,054,409 B2 | 5/2006 | Ross et al. | |
| 7,078,702 B2 | 7/2006 | Ringermacher et al. | |
| 7,098,460 B2 | 8/2006 | Lyons et al. | |
| 7,105,826 B2 | 9/2006 | Ren et al. | |
| 7,115,876 B2 | 10/2006 | Ren et al. | |
| 7,214,947 B2 | 5/2007 | Bueno et al. | |
| 7,215,801 B2 | 5/2007 | Bueno et al. | |
| 7,218,706 B2 | 5/2007 | Hopkins et al. | |
| 7,236,564 B2 | 6/2007 | Hopkins et al. | |
| 7,244,955 B2 | 7/2007 | Bueno et al. | |
| 7,280,631 B2 | 10/2007 | DeMan et al. | |

(Continued)

FOREIGN PATENT DOCUMENTS

| | | |
|---|---|---|
| JP | 06294745 A | 10/1994 |
| JP | 08160184 A | 6/1996 |

(Continued)

OTHER PUBLICATIONS

Unofficial English translation of Office Action from JP dated Aug. 6, 2013.

*Primary Examiner* — Timothy A Brainard
(74) *Attorney, Agent, or Firm* — Ann M. Agosti (57) ABSTRACT A system for inspecting nuclear fuel pellets is provided. The inspection system is configured to use X-ray radiation at one or more energies to probe nuclear fuel pellets disposed within a nuclear fuel rod for nuclear fuel pellet defects. In some implementations of the inspection system, a nuclear fuel rod manufacturing facility may be able to integrate the inspection system for fully or partially automated inspection of all fuel rods produced within the facility.

8 Claims, 5 Drawing Sheets

(56) References Cited

U.S. PATENT DOCUMENTS

| | | |
|---|---|---|
| 7,319,733 B2 | 1/2008 | Price et al. |
| 7,366,279 B2 | 4/2008 | Edic et al. |
| 7,492,855 B2 | 2/2009 | Hopkins et al. |
| 7,499,599 B2 | 3/2009 | Lokenberg Dixon et al. |
| 7,522,756 B2 | 4/2009 | Bueno et al. |
| 7,547,895 B2 | 6/2009 | Manivannan et al. |
| 7,550,754 B2 | 6/2009 | Bueno et al. |
| 7,586,252 B2 | 9/2009 | Bueno et al. |
| 7,608,829 B2 | 10/2009 | Loureiro et al. |
| 7,655,919 B1 * | 2/2010 | Shah et al. ............... 250/370.11 |
| 2006/0065844 A1 | 3/2006 | Zelakiewicz et al. |
| 2007/0248239 A1 * | 10/2007 | Mahe ........................... 382/100 |

FOREIGN PATENT DOCUMENTS

| | | |
|---|---|---|
| JP | 08505478 A | 6/1996 |
| JP | 10225454 A | 8/1998 |
| JP | 2009019963 A | 1/2009 |

* cited by examiner

NUCLEAR FUEL PELLET INSPECTION

BACKGROUND OF THE INVENTION

The present disclosure generally relates to nuclear fuel pellet inspection. More specifically, the present embodiments are directed towards X-ray methods and apparatuses for detecting physical defects in nuclear fuel pellets.

In a typical configuration, fuel for nuclear power plants is often in the form of cylindrical pellets stacked within a cladding tube. The cylindrical pellets typically contain the nuclear fuel material, and the cladding is often composed of a relatively inert substance. Together, these form a nuclear fuel rod which, during operation of the power plant, may be used to drive selected processes for power generation. One example would be steam generation that is used to power a turbine. The manufacturing of such fuel rods is typically performed by stacking the cylindrical pellets inside the cladding tube and welding end plugs onto the end of the cladding tubes.

Nuclear fuel reliability is an issue throughout the nuclear industry and is a key objective in many fuel rod manufacturing processes. Nuclear fuel pellet defects can lead to a variety of fuel performance deficiencies, among other problems. For example, pellets missing a portion of their cylindrical surface (e.g., a pit or chip), cracks, and other defects may lead to pellet-cladding interaction (PCI) in which the fuel pellet contacts the cladding resulting in stress, which may be accompanied by corrosive compounds that attack the cladding and can result in cladding rupture. Such fuel rod failures can allow highly radioactive contaminants to be dispersed in the reactor coolant. Such events can lead to higher than desired radiation exposure to power plant operators and to unplanned shutdowns of the reactor to remove and replace the failed fuel. Such unplanned outages can lead to significant financial and/or capital losses to both the energy provider and their customers.

BRIEF DESCRIPTION OF THE INVENTION

The present disclosure is generally directed to partially or substantially automated procedures for inspecting nuclear fuel pellets using X-ray radiation. In one embodiment, a system for inspecting nuclear fuel rods is provided. Among other features, the system may generally include a first X-ray source configured to produce X-ray radiation at one or more energies, the first X-ray source being disposed on one side of a moveable track configured to transport one or more nuclear fuel rods. A first X-ray detector having a first scintillator and a first diode array is also provided. The first X-ray detector is generally configured to detect at least a fraction of the X-ray radiation produced by the first X-ray source and produce a first digital X-ray image of one or more nuclear fuel rods. The first X-ray detector may be disposed on the opposite side of the moveable track from the first X-ray source. A tangible, machine-readable medium is also provided, which is generally configured to store one or more computer-implemented algorithms which, when executed by a processor, facilitate the detection of defects in one or more nuclear fuel rods using X-ray images.

In another embodiment, a method for inspecting nuclear fuel rods is provided. Among other features, the method may generally include providing a nuclear fuel rod to an inspection area, the nuclear fuel rod containing nuclear fuel pellets disposed within the nuclear fuel rod along a long axis. The nuclear fuel rod is irradiated with a first portion of X-ray radiation produced by an X-ray source. At least a fraction of the first portion of the X-ray radiation is detected with a detector generally containing a scintillator and a diode panel to produce a first digital X-ray image of the nuclear fuel rod. The nuclear fuel rod is then rotated at a first angle about the long axis using a nuclear fuel rod handling mechanism, followed by irradiation with a second portion of X-ray irradiation produced by the X-ray source. At least a fraction of the second portion of the X-ray radiation is detected, again with the detector, to produce a second digital X-ray image of the nuclear fuel rod. The first and second digital X-ray images are inspected for defects within the nuclear fuel pellets.

In a further embodiment, an imaging masking assembly is provided. The imaging masking assembly may generally include a first monolithic structure configured to be disposed proximate one side of a nuclear fuel rod having a long axis, the monolithic structure extending past the nuclear fuel rod in a direction parallel to the long axis and parallel to an X-ray beam produced by an X-ray source. The assembly may also include a nuclear fuel rod handling assembly configured to maintain the position of the nuclear fuel rod proximate the monolithic structure and configured to positionally displace the nuclear fuel rod during imaging.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION OF THE INVENTION

In a typical nuclear fuel rod manufacturing configuration, nuclear fuel pellets are inspected via visual methods during the production process. However, oftentimes several process steps must be completed subsequent to this inspection which may cause damage to the fuel pellets (among other defects). For example, because of the tight tolerances between the outer diameter of the fuel pellet and the inner diameter of the cladding rod, fuel pellets may be damaged upon insertion into the cladding. Once loaded into the cladding, handling of the fuel rods may also result in unwanted movement of the pellets within the rods, as the pellets may impact one another. Such impacts may lead to undetected defects within the fuel rods.

Accordingly, it is now recognized that substantial automation of the pellet/fuel rod inspection process using X-ray radiation as well as faster and more accurate performance of the same may be achieved by implementing the methods and apparatuses described herein. As such, the present disclosure is directed towards X-ray methods and apparatuses for detecting defects in nuclear fuel pellets.

In particular, the present disclosure utilizes X-ray sources and X-ray detectors to produce X-ray images of nuclear fuel rods (and the pellets contained inside). The X-ray sources may be configured to produce X-ray radiation at one or more energies, and the detectors may be configured to detect the same. According to an aspect of the present disclosure, the detectors may generally include a scintillator and a diode array for the production of digital X-ray images in a substantially real-time fashion. In a further embodiment, a fuel rod handling mechanism may be provided such that a number of digital X-ray images of the fuel rods may be obtained from a variety of poses to increase the probability of detecting any defects which may be present in the fuel rods or fuel pellets. According to another aspect, a processor or processing circuitry for executing stored routines (such as routines stored on a tangible, machine-readable medium) may be provided. The processor may be configured to execute one or more algorithms for the recognition, detection, and flagging of possible pellet defects. In an embodiment of this aspect, the processor may also be configured to execute algorithms to correct any image distortion resulting from random events, such as X-ray scattering arising from X-ray-pellet interactions. In certain of the embodiments generally described above, a masking fixture may also be provided to increase the image sharpness and contrast at the edges of the fuel pellets. Further, the masking structure may serve to protect the detector from unattenuated X-ray radiation that has not passed through the fuel rods.

Figure 1:
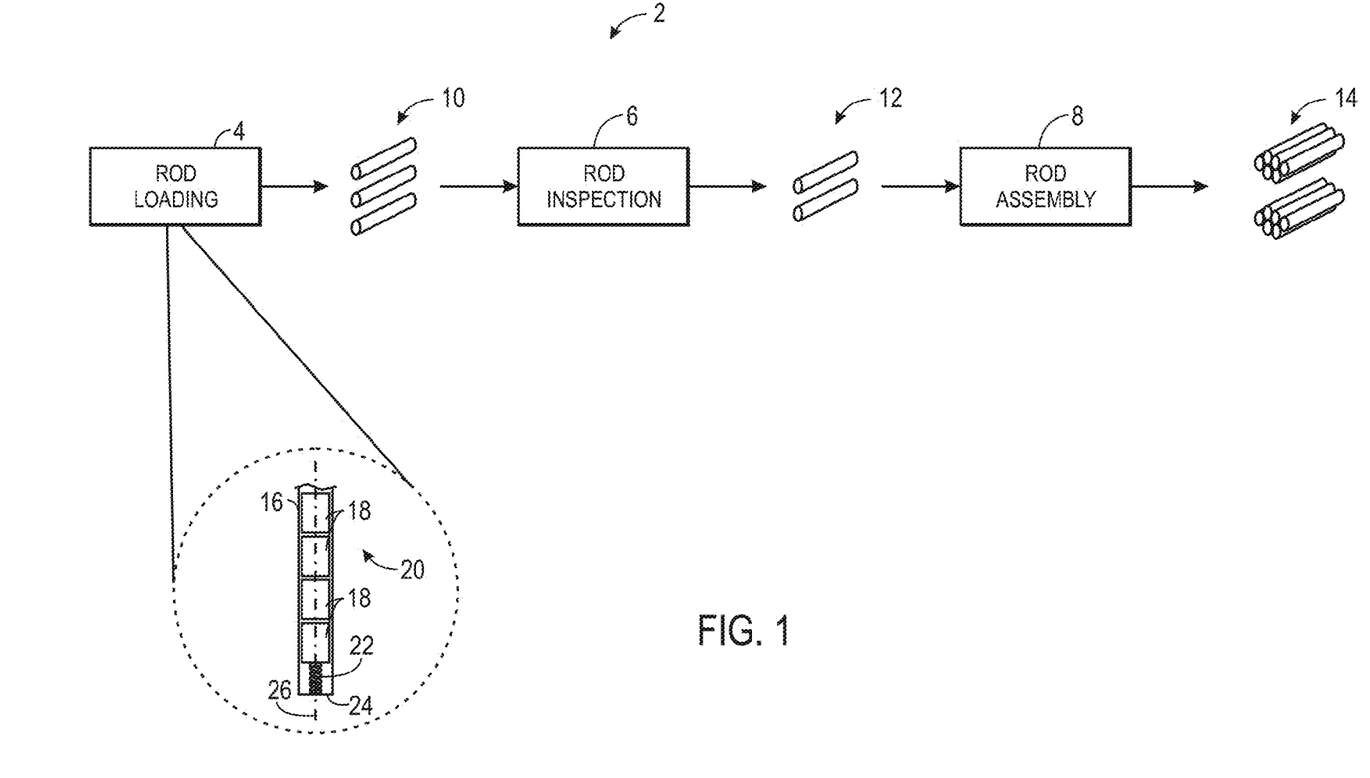
FIG. 1 is an illustration of an embodiment of a portion of a nuclear fuel rod manufacturing process, which may be modified to include certain aspects of the present disclosure.

Moving now to the figures and referring initially to FIG. 1, a block diagram illustration of an embodiment of a nuclear fuel rod manufacturing process 2 is provided, which generally includes three sections, a rod assembly section 4, a rod inspection section 6, and a bundle assembly section 8. FIG. 1 also depicts the general flow of rods through the process 2. For example, fuel rods 10 are assembled in rod assembly 4, which leads to rod inspection 6. In rod inspection 6, the number of rods 10 may be reduced to a set of inspected rods 12 (i.e., rods that have passed an inspection process). Once the rods 12 have been initially inspected, they may be passed to the bundle assembly area where the inspected set of rods 12 may be assembled into rod bundles 14. It should be noted that while the present embodiments described are directed towards the implementation of the methods and systems according to the present disclosure into one of these sections, it is well within the scope of the present disclosure to implement the approaches disclosed herein into these or other areas of a fuel rod manufacturing facility. Such implementation is within the skills of a person of ordinary skill in the art and would be a matter of routine optimization. For example, one possible implementation of the approaches described herein may be applied to substantially real-time inspection of individual nuclear fuel pellets before loading into fuel rods.

In the depicted embodiment, the process 2 begins at the rod assembly section 4. In one embodiment of rod assembly 4, hollow, long cylindrical cladding rods 16 are filled with nuclear pellets 18. However, there may be different possible configurations of a fuel rod 20, such that the pellets 18 contained within may have different patterns of placement. In some embodiments, the cladding rods 16 may be several inches to several feet long and have an internal diameter ranging from a few inches to less than an inch. According to present embodiments, the cladding rod 16 is made of a material capable of substantially isolating a nuclear fuel. For example, the cladding 16 may be a zirconium-based alloy or stainless steel, and the fuel pellets 18 may be uranium oxide ($UO_2$) or a similar nuclear fuel. In some embodiments, the fuel pellets 18 may be doped with a few percent (e.g., between about 0.5 wt % and about 10 wt %) of gadolinium oxide ($Gd_2O_3$, gadolinia) in order to absorb neutrons and allow the fuel rods 20 to exhibit more desirable reactivity characteristics. Accordingly, other neutron-absorbing materials are also contemplated.

Rod assembly 4 may include receiving fuel pellets 18 from a pellet tray, for example, using a properly configured pellet and/or rod handling mechanism. The pellets 18 are loaded into the cladding rod 16, and in some embodiments, a spring 22 is included to bias the pellets 18 against one of two end plugs 24 of the fuel rod 20. In other embodiments, this step may be performed as a separate step. The spring 22 is generally chosen and configured to bias the position of the fuel pellets 18 against an inner end surface of the fuel rod (end plug 24) to substantially limit translational movement of the pellets 18 along a long axis 26 of the fuel rod 20.

Once all of the pellets 18 have been loaded into the cladding 16 in rod assembly 4, the fuel rod 20 then undergoes a number of procedures dedicated to sealing the rod 20 and inspecting the cladding 16 for defects, generally referred to as rod inspection 6. Sealing the rod 20 may include any number of procedures known in the art, such as resistance welding and/or tungsten inert gas (TIG) welding, and is generally performed to seal both end plugs 24 onto the cladding 16. In a typical configuration, rod assembly 4 and/or rod inspection 6 may include a number of stations, including, for example, a rod type detect station, a spring check station, an evacuation/low pressure backfill station, a seam weld station, a cooldown station, a high pressure weld station, a helium leak detection station, a parallelism gage station, a ring gage station, an ultrasonic (UT) microscope station, and an unload station. It should be understood that either rod loading 4 or rod inspection 6 may include any one or a combination of these stations.

In rod inspection 6, the rods 20 are checked for any leaks of the inert gas which was used to partially backfill the rod 20 before welding on the end plugs 24. The welding seams between the cladding rod 16 and the end caps 24 may also be checked to ensure a flush, circular contact. Lastly, the rods 20, and more particularly the cladding 16, are checked for any defects. Upon inspection of the cladding 16, the rods 10 are then either accepted, rejected, or flagged for further inspection based at least in part on the integrity of the cladding 16. The rejected rods will go to a holding area, while the accepted rods 12 will be transported to the bundle assembly section 8. Any calibration and verification rods may also go to the holding area. The bundle assembly area 8 generally contains areas of scanning including passive scanning and active scanning, as well as areas where the rods 20 are actually assembled into bundles, further tested, and finally stored until delivery to a customer.

According to the present disclosure, the rod assembly 4, rod inspection 6, and/or bundle assembly 8 sections may be potential locations for implementing X-ray scanning of the fuel rods 20 into the process flow. For example, in some embodiments, X-ray inspection of the welding resulting from TIG welding processes may be used to inspect the resultant weld for integrity and quality. Accordingly, such X-ray equipment may be properly modified according to the present disclosure to allow the facile implementation of the apparatuses and methods described herein. It should be noted that in a typical manufacturing setting, tens, hundreds, or even thousands of individual rods 20 may be produced and processed every day or every few days. Accordingly, using conventional X-ray inspection processes, only a fraction of the rods 20 being produced may be inspected due to the time constraints associated with conventional radiographic inspections. For example, conventional X-ray inspection of individual rods 20 may require a total time of five or more minutes per rod 20, including the time taken to acquire the image, process the image data, and inspect the image for pellet defects. Conversely, according to the approaches described herein, it may be possible to implement direct radiography in the imaging of individual fuel rods 20, such that substantially real-time imaging and inspection of all rods produced in a manufacturing facility may be performed without negatively impacting the throughput of the facility.

Figure 2:
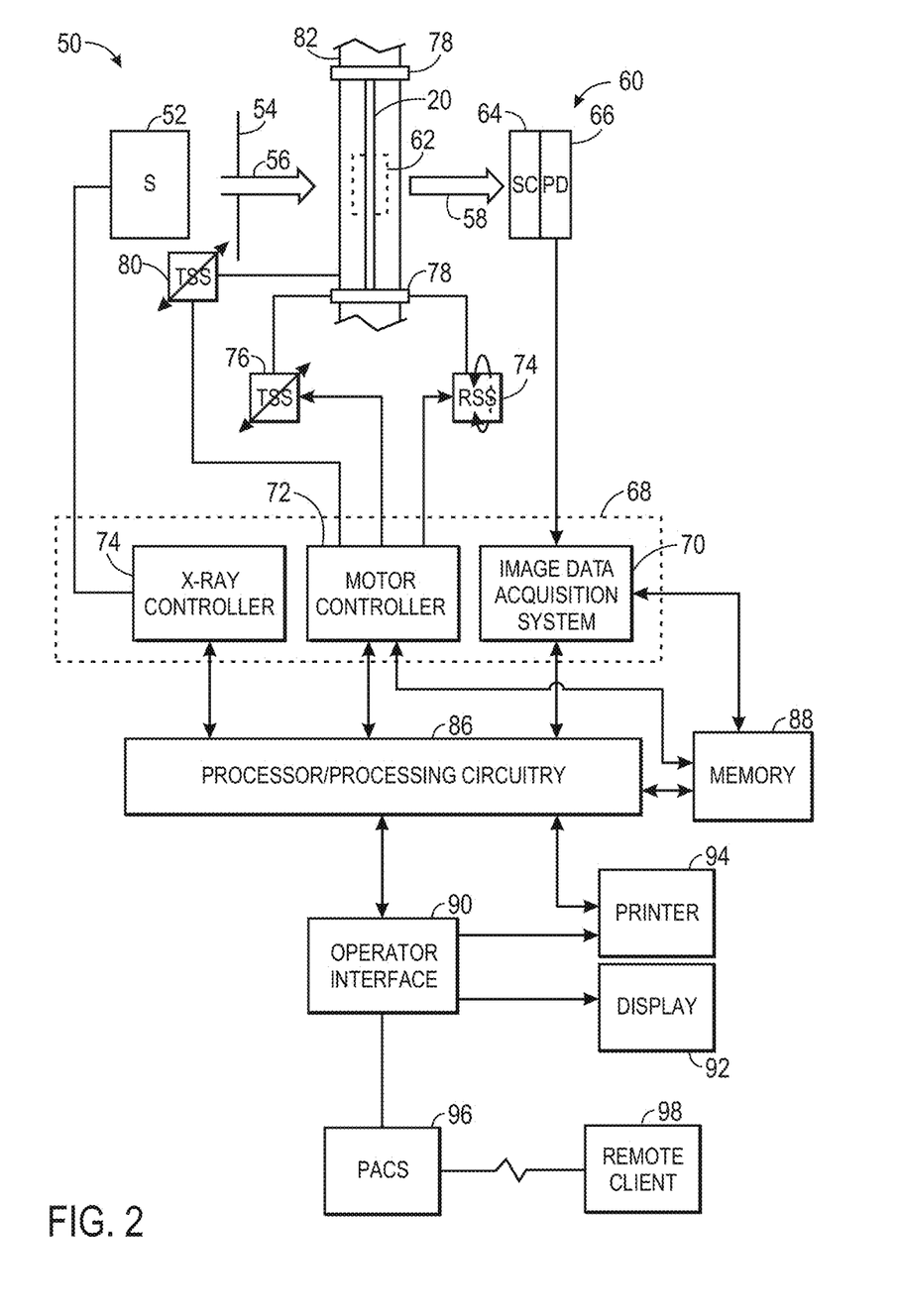
FIG. 2 is an illustration of an embodiment of a nuclear fuel inspection system, in accordance with an aspect of the present disclosure.

Such approaches may be implemented using a number of possible configurations, one embodiment of which is depicted in FIG. 2, which is a block diagram of one embodiment of a system 50 for the X-ray inspection of nuclear fuel rods, such as an individual rod 20. Of course, in some embodiments, the rods inspected may be assembled rods 10, initially inspected rods 12, or rod bundles 14. In the illustrated embodiment, the system 50 is a direct radiography system designed to acquire two- or three-dimensional digital radiography data about nuclear fuel rods and, in some embodiments, to process such data to determine the presence of any pellet defects (quality excursions) in a substantially real-time fashion (e.g., in less than five minutes, less than three minutes, less than a minute, less than thirty seconds, less than ten seconds, less than a second, and so forth). While the present discussion is directed towards the implementation of digital or direct radiography (DR) to determine pellet defects, the use of computed radiography (CR) and/or computed tomography (CT) is also contemplated, and is merely a matter of design choice. Further, the implementation of computed radiography and/or computed tomography in place of direct radiography could be accomplished with routine experimentation and optimization.

In the embodiment illustrated in FIG. 2, the system 50 generally includes an X-ray source 52 positioned adjacent to a collimator 54. The X-ray source 52 may be an X-ray tube or a solid-state X-ray emitter, and may be configured to emit X-ray radiation at one or more energies. In the embodiment depicted, the collimator 54 is configured to permit a stream of radiation 56 to pass into a region, such as an area where one or more fuel rods 20 are present. In certain embodiments, the stream of radiation 56 may have an energy sufficient to penetrate the nuclear fuel rod 20. For example, the stream of radiation 56 may have energies ranging from about 50 kV to about 1 MV (e.g., about 200 kV, 250 kV, 300 kV, 380 kV, 420 kV, 450 kV, and above, or any ranges in between). Further, the particular energy used for the stream of radiation 56 may be chosen depending on the nature of information that is to be collected. For example, lower energies (e.g., between 200 and 450 kV) may provide surface information about the pellets 18 within the fuel rods 20 (e.g., pits and/or chips), while higher energies (e.g., above about 420 kV) may provide non-surface information (i.e., cracks, etc.) about the pellets 18.

During operation, a portion of the radiation 58 passes through or around the rod 20 (or bundle of rods 14) and impacts a detector array 60. According to the present disclosure, a masking structure 62 may be provided to substantially limit the amount of radiation 56 that bypasses the fuel rod 20, and to increase the quality of the image that results from the detection of the portion of radiation 58. For example, as depicted, the masking structure 62 extends in the direction of X-ray propagation beyond the fuel rod 20. In such a configuration, the masking structure 62 may substantially limit scattering events that result from the interaction of the stream of radiation 56 and the fuel rod 20 (including the cladding 16 and pellets 18). In one implementation the masking structure 62 is configured to be disposed proximate the fuel rod 20 on one or both sides, though not directly in between the rod 20 and the source 52 or detector 60. The masking structure 62 may, in some embodiments, extend out in other directions as well, such as perpendicular to the general beam direction, to protect the detector 60 from unmitigated X-ray radiation. These and other features regarding the masking structure 62 are described in more detail hereinbelow.

During operation, upon the X-ray radiation 58 passing through the rod 20 and past the masking structure 62, detector elements of the array produce electrical signals that represent the intensity of the incident X-ray beam (fraction or portion of radiation 58). For example, the illustrated detector 60 includes a scintillator 64 and a photodiode array 66. The scintillator 64 is configured such that the X-ray radiation 58 is converted from ionizing radiation to light (i.e., visible light). The light produced by the scintillator 64 then interacts with the photodiode array 66 to produce an electric current, such as via a photovoltaic effect. In order to produce the photovoltaic effect, the diode array 66 may be constructed from a material exhibiting photovoltaic properties. For example, in one embodiment, the diode array 66 may be an amorphous silicon flat panel with a coupled field effect transistor (FET). In some embodiments, the scintillator 64 may be configured to absorb a substantial amount of the fraction of radiation 58, which may have energies between about 50 kV and 1 MV.

In one embodiment, the scintillator 64 may be constructed from thallium-doped cesium iodide (CsI:Tl) or other scintillation material that does not exhibit appreciable hygroscopicity. In such an embodiment, the CsI:Tl may be grown directly onto the diode array 66 (amorphous silicon) and then hermetically sealed with a cover plate to reduce the effects of hygroscopicity. As such, it may be possible to tailor the thickness of the scintillator 64 (the scintillating layer) to desired heights. As an example, the CsI:Tl may be grown to between about 0.050 mm to about 4 mm (e.g., about 0.40 mm, 1.0 mm, 1.5 mm, 2.0 mm) in thickness. In some embodiments, when choosing a thickness for the scintillator 64, an operator may consider a number of factors. For example, thicknesses of up to about 10 mm may be achieved by growing CsI:Tl needles onto an amorphous silicon panel. While such thickness may impart greater signal-to-noise ratios than would otherwise be achieved using shorter needles, greater scintillator thickness (e.g., over 4.0 mm) may lead to reduced contrast around the edges of the pellets 18 and thus, lowered spatial resolution of pellet defects. However, there may be embodiments or situations where such lengths are desirable and an increase in contrast resolution achieved with a thicker scintillator may outweigh the decrease in its spatial resolution for the detection of these defects.

In another embodiment, the scintillator 64 may be constructed from polycrystalline terbium-doped gadolinium oxysulfide ($Gd_2O_2S$:Tb) phosphor sheets. In such an embodiment, particles of $Gd_2O_2S$:Tb are mixed with a binder and adhered to a polymeric (e.g., Mylar) support. When $Gd_2O_2S$:Tb phosphors are used, the particles with binder may form sheets having a thickness between about 0.050 mm to about 2 mm (e.g., about 1 mm). In certain embodiments where a phosphor is used, it may be desirable to use, in lieu of or in combination with $Gd_2O_2S$:Tb, terbium-doped yttrium oxysulfide ($Y_2O_2S$:Tb), silver-doped zinc sulfide-cadmium sulfide alloy (ZnSCdS:Ag), or similar phosphor, or any combination thereof. Other phosphors may include those employing copper-doped zinc sulfide (ZnS:Cu), copper-doped zinc-cadmium sulfide (ZnCdS:Cu) and similar phosphors using aluminum dopants, to name a few. A choice of any related phosphor known in the art is merely one of design and should be readily apparent to those of skill in the art and is considered to be within the scope of this disclosure.

In a further embodiment, it may be desirable to use fiber optic scintillating glass to construct the scintillator 64. In a typical configuration of fiber optic glass, a core fiber is the scintillating material (e.g. a terbium-doped heavy silicate glass of moderate effective atomic number and density), which is surrounded by a cladding glass that allows light to propagate down the fiber toward one or more photodiode arrays 66. In such embodiments, the fiber/cladding is close-packed into a faceplate of many millions of fibers (e.g., between about 1 and about 20 million), with a total thickness (length of cladding glass) of between about 1 mm and about 10 mm (e.g., about 2 mm). The fiber optic scintillating glass faceplate may also include extramural absorbing material, either surrounding the cladding, or placed in a statistical manner as individual fibers throughout the faceplate. Both methods may be used to block stray light that exits fibers from reaching the diode structure below.

Thus, the scintillator 64 may be constructed from a number of materials designed to emit light to the photodiode array 66 upon absorbing ionizing radiation. The scintillator 64, as mentioned, has a thickness of between about 200 microns to about 10 millimeters, with the thickness being chosen based on a number of factors including the type and material of the fuel rod 20, geometry of the defect, the energy of the emitted X-ray radiation 56, and so forth. The scintillator 64 may have tens, hundreds, thousands, or even millions of rows of needles and/or detector elements. In one embodiment, by decreasing the size and increasing the number of the needles in the scintillator 64, the resolution of a resultant image may be increased. In embodiments where the scintillator 64 has a high resolution, the resolution of a resultant digital X-ray image may be limited by the resolution of the photodiode array 66. For example, as mentioned, the photodiode array 66 may be a flat panel of amorphous silicon. In one embodiment, the amorphous silicon panel may have a resolution of about 1024 by 1024 over a 16-inch by 16-inch area. In another embodiment, it may have a resolution of about 2400×3000 over a 9.4-inch by 11.8-inch.

The process of generation of light by the scintillator 64, its transfer to the diode array 66, and the generation of a digital image by the array 66 may occur within a fraction of a second, e.g., in near-real time. Therefore, the direct radiography configuration according to present embodiments may allow substantially real-time imaging of the rod 20, with imaging speeds of up to about 30 Hz being attainable. As a result, imaging and inspection of a rod 20 may be performed in a matter of seconds. For example, inspection of a rod 20 may occur in under 3 seconds, 5 seconds, 10 seconds, 30 seconds, 1 minute, 3 minutes, 5 minutes and so forth. Accordingly, the implementation of direct radiography into a manufacturing process, such as the manufacturing process 2, may permit all or a majority of the individual rod 20 that are produced to be inspected, rather than inspecting on a selective, random or subset basis. In operation, once the photodiode array 66 generates electrical signals corresponding to the numbers of X-rays that have passed through the rod 20, the signal is passed to a system controller 68, and more particularly, to an image data acquisition system 70 that is configured to receive and/or process the signals generated by the detector 60.

The system controller 68 is configured to control the X-ray source 52, and furnishes both power and control signals for rod inspection procedures. Moreover, the detector 60 is coupled to the system controller 68, which commands acquisition of the signals generated in the detector 60. The system controller 68 may also execute various signal processing and filtration functions, such as for initial adjustment of dynamic ranges, interleaving of digital image data, and so forth. In general operation, system controller 68 commands operation of the imaging system 50 to execute inspection protocols and, in some embodiments, to process acquired data. In the present context, system controller 68 also includes signal processing circuitry, typically based upon a general purpose or application-specific digital computer, associated memory circuitry for storing programs and routines executed by the computer (such as programs and routines for implementing the embodiments described herein), as well as configuration parameters and image data, interface circuits, and so forth.

In the embodiment illustrated in FIG. 2, the system controller 68 contains a motor controller 72, which is configured to control a rotational subsystem 74 and a translational subsystem 76 of a rod positioning system 78. The rod positioning system 78 is configured to allow an operator or controller to move the rod 20 translationally along its long axis 26 and/or rotationally about its long axis 26. Such positioning may be useful in detecting pellet defects, as certain defects may only be imaged and thus visible from one pose of the rod 20 with respect to the X-ray source 52 and the detector 60. Further, the rod positioning system 78 may be useful in some aberration correction methods (e.g., shift imaging) performed by the system controller 68, which is described, along with other implementations of the present disclosure, hereinbelow.

As depicted, the rod positioning system 78 may perform the translation and/or rotation by clasping on to one or both ends of the fuel rod 20. The rotational subsystem 74 allows the rod positioning system 78 to then rotate the rod 20 about its long axis 26, either in a smooth, continuous rotation or in a step-and-shoot manner, where the rod 20 is rotated at an angle, an image is taken, and the rod 20 is then rotated again for subsequent image capture. Accordingly, the rotation performed by the rod positioning system may be between about 90° and about 1° (e.g., about 90, 55, 45, 22.5, 11.25 degrees). In certain embodiments, the rod positioning system may also perform small rotations of less than 10°, for example less than about 9, 8, 7, 6, 5, 4, 3, 2, or 1 degree. Similarly, the translational subsystem 76 may allow the rod positioning system 78 to perform a small translation along the long axis 26 of the rod 20, the translation being only to a small extent (i.e., between about 1 micron and several centimeters).

To this end, the motor controller 72 is also configured to control a translational subsystem 80 of a moveable track 82, along which the rod 20 (or a bundle of rods 20) rests. The moveable track 82 may be configured to move in small (e.g., about 1 foot) or in large (e.g., about 15 foot) increments, or in a continuous fashion depending upon the throughput of the system 50 and particular application-specific design choices. For example, the moveable track 82 may translate the rod 20 along its long axis 26 after a required number of images have been taken of a particular section of the rod 20 (e.g., a section of a few pellets). In such an embodiment, the moveable track 82 would translate the rod 20 such that a new section within the same rod 20 (e.g., a new section of a few pellets) would be imaged by the X-ray source 52 and detector 60. Further, the moveable track 82 may serve to transport the rod 20 (or rod bundle(s)) out of the area defining the inspection system 50.

The system controller 68 may coordinate the timing of the actuation of the rod positioning system 78 and the moveable track 82 with the X-ray source 52 and the detector 60. As such, the system controller 68 may control the X-ray source 52 with an X-ray controller 84. Particularly, the X-ray controller 84 may be configured to provide power and timing signals to the X-ray source 52. For example, in one embodiment, the X-ray controller 84 may provide the proper power to the X-ray source 52 to probe the rod 20 for surface defects. In addition, the X-ray controller 84 may provide a different amount of power to the X-ray source, such that the rod 20 is probed for non-surface defects, such as cracks in the pellets 18, and the like.

The system controller 68, in the embodiment illustrated, also includes processing circuitry 86. The data collected by the image data acquisition system 70 may be transmitted to the processing circuitry 68 for subsequent X-ray image manipulation and inspection. The processing circuitry 86 may include (or may communicate with) a memory 88 that can store data processed by the processing circuitry 86 or data to be processed (such as digital X-ray images produced by the imaging of the rod 20) by the processing circuitry 86. It should be noted that any type of computer accessible memory device capable of storing the desired amount of data and/or code may be utilized by the imaging system 50. Moreover, the memory 88 may include one or more memory devices, such as magnetic, solid state, or optical devices, of similar or different types, which may be local and/or remote to the system 50. The memory 88 may store data, processing parameters, and/or computer programs (e.g., image recognizing and manipulating algorithms) having one or more routines for performing the processes described herein. For example, in one embodiment the memory 88 may store X-ray inspection software. The software may contain code configured to acquire, report, review, and archive information about the rod 20. For example, during operation, the code may allow the processing circuitry 86 to interact with the inspection equipment (X-ray source 52 and detector 60) to collect digital information. The code may contain a database of relevant inspection implementations and/or protocols and may be configured to control the inspection equipment. The software may also accept acquired data and removable media, such as CD and DVD, as well as provide application tools for analysis, enhancement, measurement, and storage of received data. An example of such software is the Rhythm Software Suite produced by GE Inspection Technologies.

The processing circuitry 86 may be configured to control features enabled by the system controller 68, e.g., inspection operations and rod movement. For example, the processing circuitry 86 may be configured to receive commands and inspection parameters from an operator via an operator interface 90 typically equipped with, for example, a keyboard, mouse and/or other input devices. An operator may thereby control the system 50 via the input devices. A display 92 coupled to the operator interface 90 may be utilized to observe digital X-ray images of the rod 20 (and thus the pellets 18). Additionally, an image may be printed by a printer 94, which may be coupled to the operator interface 90. In some embodiments, one or more operator interfaces 90 may be linked to the system 50 for outputting system parameters, requesting inspection, viewing images, and so forth. In general, displays, printers, workstations, and similar devices supplied within the system 50 may be local to the data acquisition components, or may be remote from these components, such as elsewhere within a manufacturing facility, or in an entirely different location, linked to the image acquisition system via one or more configurable networks, such as the Internet, virtual private networks, and the like.

The processing circuitry 86 may also be coupled to a picture archiving and communications system (PACS) 96. Image data generated or processed by the processing circuitry 86 may be transmitted to and stored at the PACS 96 for subsequent processing or review. It should be noted that PACS 96 might be coupled to a remote client 98, or to an internal or external network, so that others at different locations may gain access to the image data (e.g., a customer who purchases the rods 20).

Figure 3:
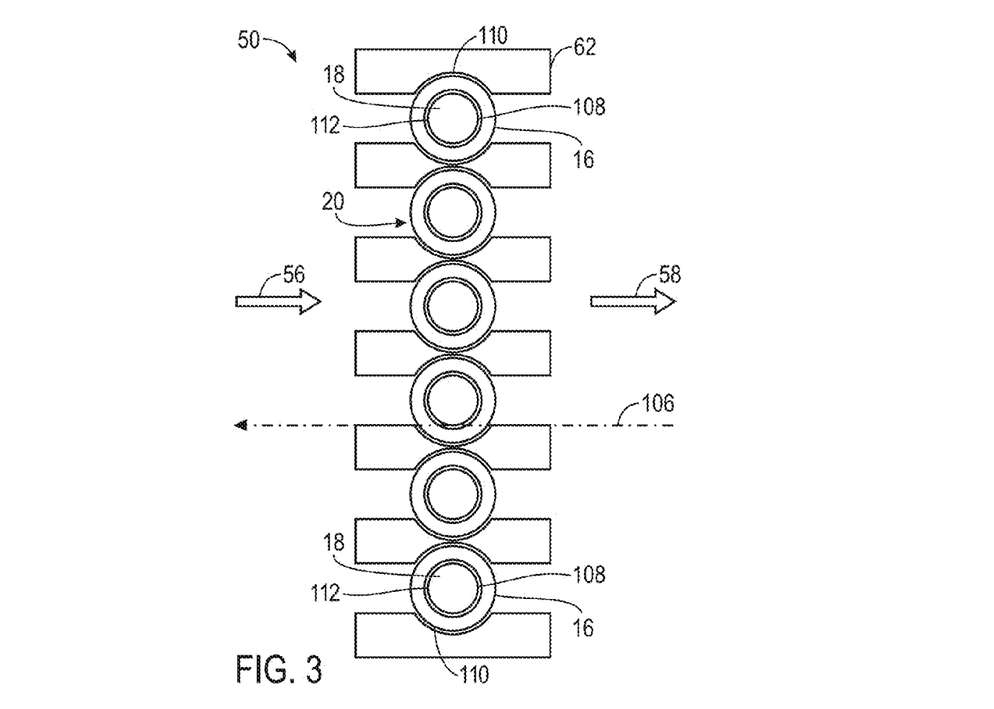
FIG. 3 is an illustration of an embodiment of nuclear fuel rods disposed within an imaging masking structure, in accordance with one aspect of the present disclosure.

Moving now to FIG. 3, an embodiment of a masking fixture 62 is illustrated from a head-on view. FIG. 3 also illustrates the general configuration of rods 20 and their position with respect to the masking fixture 62 during imaging. For example, FIG. 3 may be considered as being viewed from a perspective perpendicular to the X-ray beam path 106 from of the X-ray source 52. For example, as depicted, beam path 106 is the general direction of X-ray propagation of X-rays 56 and portion of X-rays 58. Further depicted in the illustrated embodiment are multiple rods 20 disposed within the masking fixture 62. According to the present disclosure, it may be desirable to image as many rods 20 as possible at once, with limiting factors including the size of the detector 60, the size of the masking fixture 62, as well as the handling capacity of the rod positioning system 78 and the moveable track 82, among others. Looking down long axis 26, the rod 20 according to present embodiments contains the cladding 16 and fuel pellets 18 having a pellet surface 108. The masking fixture 62, as depicted, is disposed proximate the rods 20, such that substantially no space or only a small space 110 exists between the fixture 62 and one of the rods 20. The spacing between the rod 20 and the masking fixture 62 may be sufficient, in certain embodiments, to allow the rod 20 to freely rotate and translate about and along the long axis 26 with respect to the masking fixture 62. In one embodiment according to the approaches described herein, the masking fixture 62 may curve around the rod 20, such that the cladding 16 of the rod 20, or more specifically a surface of the cladding 16 having a tangential relationship to beam path 106, is substantially masked, allowing only the pellets 18 and surface of the pellets 108 to be imaged. Additionally, a tolerance 112 between the pellets 18 and the cladding 16 may allow a higher contrast with regard to the surface of the pellets 18, such that a an inspection routine may more efficiently identify any pellet defects and/or abnormalities.

To substantially limit the amount of radiation that passes by the rods 20, it may be desirable for the masking assembly 62 to be constructed from one or more high Z elements. In one embodiment, the masking assembly 62 is a monolithic structure made of tungsten (W). High Z elements are those elements with a large atomic number, and for the purposes of the present disclosure, high Z elements consist of those elements with an atomic number greater than or equal to 74. In one embodiment the masking assembly 62 contains little or substantially no other materials which may impede the ability of the masking assembly 62 to absorb X-ray radiation. Therefore, the masking assembly 62, in one embodiment is constructed only from elements such as tungsten and high Z-value elements, with the only other materials present in the masking fixture 62 being impurities from the purposely included elements. In another embodiment, it may be desirable to construct the masking fixture 62 such that a lighter weight material (e.g., a polymer) is encapsulated within an outer shell of a high-Z material, such as tungsten. In such an embodiment, the masking fixture may retain its X-ray absorption properties while having a lighter weight than would otherwise be achieved.

Figure 4:
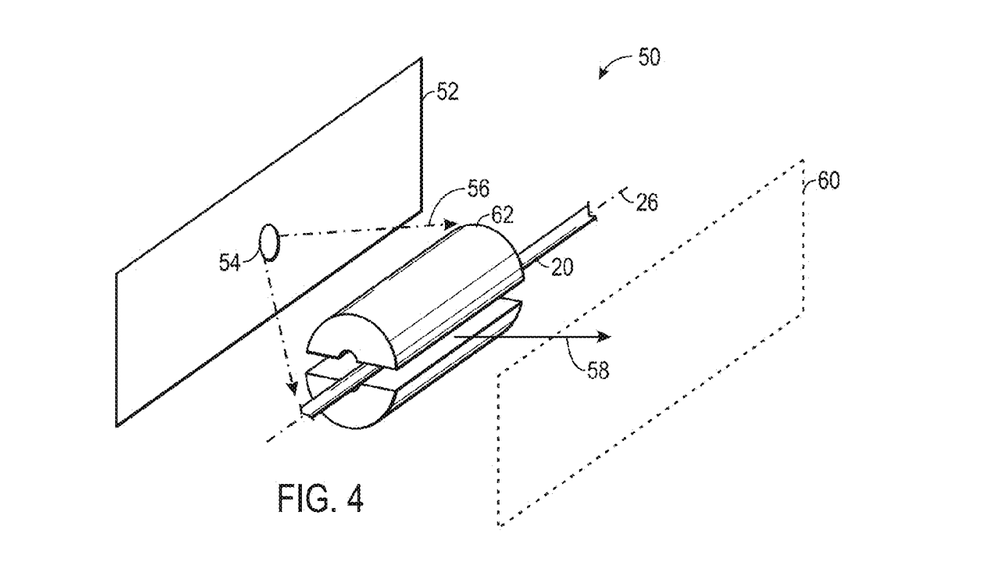
FIG. 4 is a perspective view illustration of an embodiment of a nuclear fuel rod disposed within an imaging masking structure, in accordance with one aspect of the present disclosure.

A perspective view of the masking fixture 62 during operation of the system 50 is illustrated in FIG. 4. In accordance with the present disclosure, the illustrated embodiment depicts the masking fixture 62 as being disposed between the X-ray source 52 and the detector 60. Further depicted is a representation of the radiation 56 which emanates from the X-ray source 52 and out of the beam collimator 54. A portion of the X-ray radiation 56 passes through the rod 20 (radiation 58), and another portion of the X-ray radiation 56 strikes the masking assembly 62. The masking assembly 62, in the depicted embodiment, includes two monolithic structures placed on either side of the rod 20, and the two monolithic structures extend past the rod 20 towards the X-ray source 52 and the detector 60. Such a configuration where the masking structure 62 extends past the rod 20 may substantially limit the amount of scattered radiation that reaches the detector 60 as a result of non-absorptive interactions between the rod 20 and the incident radiation 56.

Figure 5:
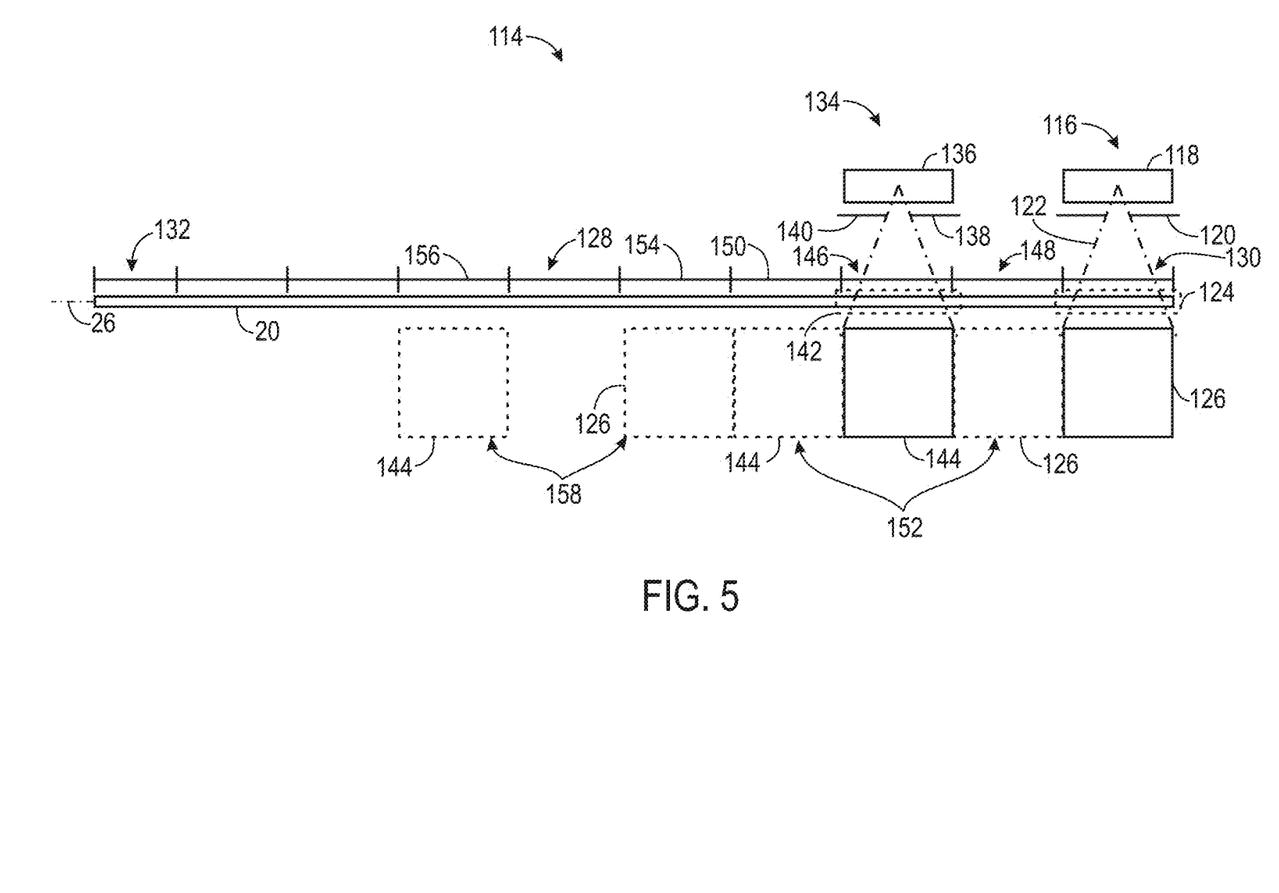
FIG. 5 is an illustration of an embodiment of a section of a nuclear fuel inspection system, the inspection system including two or more X-ray sources and X-ray detectors, in accordance with an aspect of the present disclosure.

Moving now to FIG. 5, an embodiment of a system 114 employing more than one X-ray source 52 and more than one detector 60 is illustrated. In the depicted embodiment, the system 114 includes an X-ray source-detector combination 116 having the X-ray source 52 (e.g., a first X-ray source 118), the collimator 54 (e.g., a first collimator 120) which controls an amount of radiation 122 that is incident onto the rod 20, and the masking fixture 62 (e.g., a first masking fixture 124) which is configured to protect the detector 60 (e.g., a first detector 126) and limit X-ray scattering off of the rod 20. Further depicted in FIG. 5 are sections of the rod 20, generally denoted using numeral 128, which are imaged one at a time. For example, the first collimator 120 may control the width of the radiation beam 122 to cover a first section 130 of the rod 120. Further, the first detector 126 may have a width slightly larger than the width of the first section 130 (and most subsequent sections) as a result of the X-ray radiation 122 having a fan or cone-shaped beam. For example, the width may be between about ⅛ inch and 5 inches greater in width than the sections 128. As such, the overall features contained within the rod 20 (e.g., the pellets 18) may be inspected by dividing the rod into the sections 128 and imaging each section 128 in sequence. It should be noted that the masking fixture 62, as well as the imaging equipment may be fixed in place, with the rod 20 being moved translationally along the moveable track 82 and rotated using the rod positioning system 78, both of which are described with regard to FIG. 2. In one embodiment, for example, the moveable track 82 may move the rod 20 along its long axis 26 by a length substantially equal to that of the width of sections 128.

In some embodiments, by adding more than one source-detector combination, the throughput of inspection of the fuel rods 20 may be increased, as fewer sections 128 may need to be imaged by a single source-detector combination. For example, a typical fuel rod length is about 14 feet. In some embodiments, the fuel rod 20 may be divided equally over the length of 14 feet, with each section 128 being on the order of the width of the detector 60 (e.g., about 16 inches, with the detector being slightly larger). Thus, the rod 20 may be divided into about 11 sections 128 having about a 16-inch width with a smaller 4-inch section 132 remaining, for a total of about 12 sections. Thus, one X-ray source-detector combination would have to perform 12 different inspection sequences. However, by using more than one properly-spaced source-detector combination, the number of required inspection sequences may decrease. In some embodiments it may be desirable to have two X-ray source-detector combinations side-by-side, such that two consecutive sections 128 may be imaged substantially simultaneously. Three combinations which are side-by-side may image three consecutive sections 128, and so on. While multiple source-detector combinations may be useful, the capital cost of equipment as well as the floor space needed for the equipment that accompanies each combination (e.g., chillers and power supplies) may also be a consideration. Further, the imaging equipment as well as the accompanying chillers, power supplies, and so forth may limit the ability to place the combinations directly adjacent to one another (e.g., within less than 16 inches of one another). As such, according to the present disclosure, the first X-ray source-detector combination 116 may be accompanied by one or more additional X-ray source-detector combinations (e.g., a second X-ray source-detector combination 134), with an integer number of approximately one section 128 length(s) in between each combination. As illustrated, the additional X-ray source-detector combinations contain similar equipment and configurations to that of the first X-ray source-detector combination 116, and generally includes the X-ray source 52 (e.g., a second X-ray source 136) and the beam collimator 54 (e.g., a second beam collimator 138) that is configured to control the shape and area of an X-ray beam 140 during operation. The masking fixture 62 (e.g., a second masking fixture 142) is provided which is configured to substantially limit scattering and bypass radiation, and the detector 60 (e.g., a second detector 144) is provided to produce digital X-ray images of a second section 146 being imaged.

According to the present disclosure, including multiple X-ray source-detector combinations (116, 134) within the pellet inspection system 114 may yield a number of possible configurations. For example, the first X-ray source-detector combination 116 may be configured to perform tangential imaging (imaging of surface defects) of the pellets 18 within the fuel rod 20, while the second X-ray source-detector combination 134 may be configured to perform non-tangential imaging (imaging of deeper defects, such as cracks) of the pellets 18 within the fuel rod 20, and/or vice-versa. In one embodiment, such configurations may be accomplished by configuring the first X-ray source 118 to generate X-ray radiation 122 having an energy less than about 450 kV. As such, the second X-ray source 136 may be configured to generate X-ray radiation 140 having an energy greater than about 450 kV. Accordingly, it may be possible to configure system 114 such that one X-ray source-detector combination performs a certain type of scan (e.g., tangential), while the other performs a different type (e.g., non-tangential). Either combination 118, 136 may perform either mode of scanning, the choice of which may be purely one of design and throughput.

In another embodiment, the system 114 may be configured such that the number of inspection sequences is decreased by performing non-tangential and tangential imaging together using a single X-ray source-detector combination (118 or 134), with each combination (118 or 134) performing inspection sequences on different sections 128. In such an embodiment, the first combination 116 may perform an inspection sequence on section 130, followed by an inspection sequence on section 148 (the adjacent section). Accordingly, the second combination 134 may perform an inspection sequence on section 146, followed by an inspection on section 150. Such movement is depicted in FIG. 5 as dashed boxes representative of the positions of the detectors 126, 144 at a second position 152. Of course, to avoid dual-inspection of section 146, the rod 20 may be moved translationally (by the moveable track 82, for example) over a length substantially equal to three times the width of one of the sections 128, such that in a third sequence, the first combination 116 inspects section 154 and the second combination 134 inspects section 156 at a third position 158. Other configurations may be possible using multiple X-ray source-detector combinations, and are considered to be within the scope of this disclosure.

Figure 6:
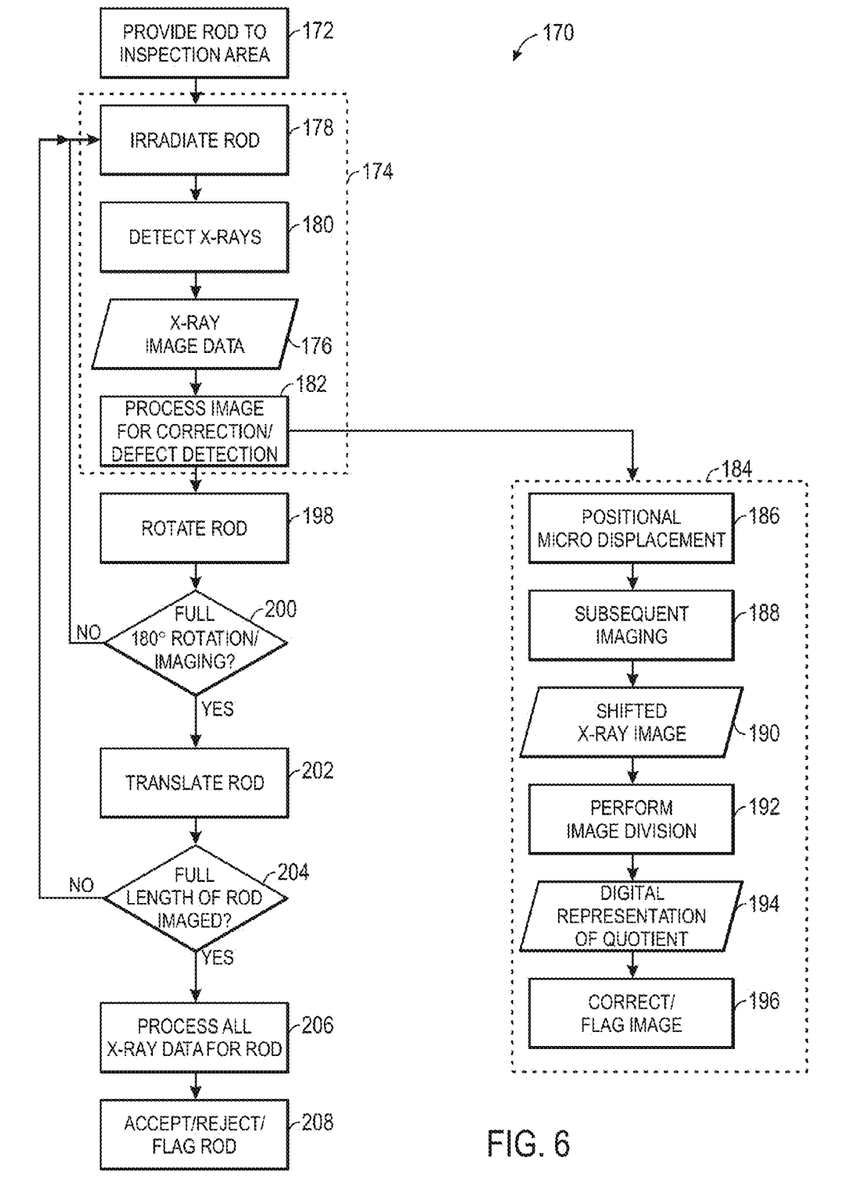
FIG. 6 is an illustration of a method of inspecting nuclear fuel rods using features of the nuclear fuel inspection system of FIGS. 2-4, in accordance with an aspect of the present disclosure.

The systems described above may be used singularly or in combination with one another using the flow chart illustrated within FIG. 6, which is a flow-chart depicting an embodiment of a method 170 for inspecting fuel pellets 18 in accordance with the present disclosure. Method 170 may be performed by a system controller, such as the system controller 68, or a human operator, or a combination of both, as will be apparent from the following description. Method 170 includes, among other features, providing (block 172) the rod 20 (or bundles of rods 20) to an inspection area (such as the inspection systems 50, 114). The rod or rods 20 may be provided, for example, by the moveable track 82 and/or the rod positioning system 78. In some embodiments, only a portion of the rod 20 (or bundle of rods 20) may be provided to the inspection area, such as that described in FIG. 5. In one embodiment, for example in an automated routine, the system controller 68 may direct the moveable track 82 to provide the rod 20 or the section 128 of the rod 20 to the inspection area, such that the system controller 68 may begin an imaging sequence. In another embodiment, a human operator may, for example, engage the moveable track 82 to perform the same action.

Once the rod 20 has entered into the inspection area, a human operator or the system controller 68 will engage the system 50, 114 to begin a subset of imaging (block 174). As illustrated, the set of imaging steps generally includes a number of steps that are used to eventually generate a digital X-ray image 176 of the rod 20. The imaging steps may begin with irradiation (block 178) of the rod 20. The irradiation may be performed by the X-ray source 52 where the system controller 68 may direct the X-ray controller 84 to provide a certain power level to the X-ray source 52. The power level provided may be selected for tangential or non-tangential imaging of the rod 20, and as mentioned may be anywhere between 50 kV and up to 10 MV (e.g., between about 120 kV and 420 kV, or between about 450 kV and 1 MV). Once the rod 20 has been irradiated (block 178), the radiation that passes through the rod 20 (e.g., radiation 58) is detected by the detector 60 (block 180). For example, in the embodiments described where the detector 60 includes the scintillator 64 and the diode array 66, the radiation that passes through the rod 20 may be absorbed by the scintillator 64, where the scintillator generates light that is passed to the diode array 66. The diode array 66 then converts, through a photovoltaic effect, the light from the scintillator 64 into electrical signals, which may be amplified and digitized by a transistor, such as a field-effect transistor disposed onto the diode array 66, which generates the digital X-ray image data 176.

To complete the imaging steps, the digital X-ray image 176 may be directed to the image data acquisition system 70 and eventually to the processing circuitry 86 for processing the image data to detect pellet defects (block 182). For example, the processing circuitry 86 may execute code stored in memory 88 directed to the recognition of pellet abnormalities and similar features. The X-ray controller 84, having directed the X-ray source 52 to emit X-ray radiation at a discrete energy level (or range), may provide the processor 86 with such information, such that the code is executed in a manner where the defect detection is focused on surface defects of the pellets 18 or on non-surface defects of the pellets 18. Further, the processor 86 may execute (block 182) code configured to correct any abnormalities within the digital X-ray image 176. For example, the digital X-ray image 176 may have one or more bright spots or areas that result from X-ray scattering due to interactions of the incident X-ray beam with the rod 20 or other features.

In an embodiment, the system controller 68, if the processor 86 detects such abnormalities in the digital image 176, may start a shift imaging routine 184. In such an embodiment, the system controller 68 may direct the rod positioning system 78 to perform a positional micro-displacement step 186. To perform positional micro-displacement, the rod positioning system 78 may move the rod 20 by rotating the rod 20 about its long axis 26 at an angle that is substantially smaller than that used for imaging the entire circumference of the pellets 18, which is described hereinbelow. Alternatively or additionally, the rod positioning system 78 may translate the rod 20 along its long axis 26 by a length on the order of a few microns to a millimeter (e.g., about 1 microns to about 1 millimeter). The system controller 68 may then direct the system 50 to perform subsequent imaging steps 174 (block 188) to produce a digital image 190 which is slightly shifted from the digital X-ray image 176. In some embodiments, the processor 86 may then execute code stored in memory 88 that is configured to correlate each image with the other (e.g., correct for the micro-displacement via registration of the two images) and divide (block 192) the digital image 176 by the digital image 190, or vice-versa. In other embodiments, no digital shift of pixels may be necessary. Such embodiments may arise when the positional micro-displacement 186 is on the order of the width of a pellet defect, which may allow scatter and background to be subtracted and/or normalized, resulting in the acquisition of defect information. The division may be performed such that each pixel of one image is divided by the same pixel in another image. The quotient is represented as a digital representation 194, which may be a digital map of the digital image 176, where areas (pixels) are represented as a number. For those pixels (or sets of pixels) that have a value that is not one, this may represent a defect in a pellet 18 or a scattering event. Thus, the shift imaging sequence 184 may be useful for defect detection in addition to image correction (block 196).

In one embodiment of imaging correction and/or flagging, the processor 86 may be able to distinguish defects in the pellets 18 from scattering events by pattern recognition. For example, the memory 88 may contain a database of common shapes or artifacts observed when the pellet 18 exhibits a defect. The processor 86 may compare an area of similar non-unitary numbers within the digital representation 194 against the database. If the area matches a database shape, then the digital image 176 may be flagged for the presence of a possible defect. Conversely, if the area does not match a database shape, or if the area is on the order of a single pixel, the processor 86 may correct the area using, for example, an anti-aliasing algorithm. This process may be performed over any area within the digital representation 194, which may result in the correction and/or flagging of the digital image.

Once processing and optional shift imaging are complete, the rod 20 may be rotated about its long axis 26 at an angle (block 198) in order to image a different portion of the pellets 18 (block 200), the imaging generally including imaging steps 174. Imaging of the different portion or section of the pellets 18 may be performed during the inspection process, in some embodiments, using the rod positioning system 78. For example, the system controller 68 may direct the rod positioning system 78 to rotate the rod 20 at a given angle. The angle of rotation may be selected for a number of reasons, including the desired time allotment for imaging a section of the rod 20, the mechanical limitations of the rod positioning system 78, the requirements of the processing circuitry 86 that may be used to process image data, and the energy that is used to image the pellets 18 to name a few. For example, in some embodiments, the angle may be between 11.25° and 90° (e.g., about 11.25°, 22.5°, 45°, or 90°), such that the number of times step 198 is performed is directly dependent upon the number of rotations necessary at the chosen angle to eventually perform a full 180° rotation. In one embodiment, the angle may be about 11.25°, such that 16 rotations may be necessary to complete a full 180° rotation. In some embodiments, it may be desirable to have a relatively small angle of rotation (e.g., 11.25° or 22.5°) in order to increase the probability of detecting a defect in the pellets 18. In another embodiment, the rod positioning system 78 may continuously rotate the rod 20 about its long axis. In such an embodiment, the system 50, 114 may operate on a substantially real-time basis, with digital images being captured at a rate of about 30 Hz.

After performing rotation and imaging, a query 200 is performed to ascertain whether full 180° rotation and imaging has been completed. If the full 180° imaging has not been completed, the method 170 may cycle back to irradiation of the rod (block 178). In embodiments where full 180° rotation and imaging has been completed, the rod 20 is then translated (block 202) along its long axis 26 by the moveable track 82, such that a new section of the rod 20, having non-imaged pellets are imaged by the system 50 (block 174). Translation of the rod 20 may include a movement of anywhere from a few inches to several feet, as mentioned. In one embodiment, the length that the rod 20 is moved may be substantially equal to the width of the area of observation between the X-ray source 52 and the detector 60. As with rotation followed by imaging, a query 204 is performed to ascertain whether the full length of the rod 20 has been imaged. If the full length of the rod 20 has not been imaged, the method 170 may cycle back to irradiation of the rod (block 178). Once full imaging of the length of the rod 20 is complete, the entire rod 20 may be processed (block 206). The processing may involve processing all of the acquired X-ray image data for the sections, as well as for the entire rod 20. In certain embodiments, due to the ability to acquire substantially real-time images of the rod 20, it may be desirable to perform a three-dimensional reconstruction of the rod 20 or sections of the rod 20, such that a digital representation of the rod 20 may be stored in a database and/or reviewed by the processor 86 or human operator. In one embodiment, it may be desirable to perform such three-dimensional reconstruction on rods that contain potentially defective pellets.

In some embodiments, the processor 86 may flag (block 208) certain sections of the rod 20 or the entire rod 20, such that rods 20 that have acceptable sections may be re-worked (sent to a re-working station) and completely disassembled to salvage pellets 18 with no defects. Rods 20 that are not flagged or rejected may be sent on for further storage until they are packed and shipped to a customer.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of inspecting nuclear fuel comprising:
providing a nuclear fuel rod to an inspection area, the nuclear fuel rod comprising nuclear fuel pellets disposed within the nuclear fuel rod along a long axis;
irradiating the nuclear fuel rod with X-ray radiation to generate a series of angularly displaced images of the nuclear fuel rod via direct radiography, such that the circumference of the nuclear fuel pellets is substantially imaged;
inspecting the series of angularly displaced images to detect nuclear fuel pellet defects;
irradiating the nuclear fuel rod with additional X-ray radiation having a different energy to generate one or more additional images; and
inspecting the one or more additional images to detect different nuclear fuel pellet defects.

2. The method of claim 1, wherein the X-ray radiation used to generate the series of angularly displaced images has a lower energy than the additional X-ray radiation.

3. The method of claim 1, wherein the series of angularly displaced images are inspected to detect tangential nuclear fuel pellet defects and the one or more additional images are inspected to detect internal nuclear fuel pellet defects.

4. The method of claim 1, wherein inspecting the series of angularly displaced images comprises executing one or more comparison and/or detection algorithms using one or more algorithms to facilitate the detection of nuclear fuel pellet defects, wherein irradiation and inspection occur in less than about 30 seconds.

5. The method of claim 1, comprising reducing unattenuated X-rays incident at a detector used to generate the series of angularly displaced images by positioning a masking fixture proximate the nuclear fuel rod.

6. The method of claim 1, wherein a rod positioning mechanism is used to rotate the nucelar fuel rod to produce the series of angularly displaced images.

7. The method of claim 1, wherein a detector comprising a scintillator and a diode array is used to generate the series of angularly displaced images of the nuclear fuel rod, the images comprising digital X-ray images.

8. A method of inspecting nuclear fuel comprising:
providing a nuclear fuel rod to an inspection area, the nuclear fuel rod comprising nuclear fuel pellets disposed within the nuclear fuel rod along a long axis;
irradiating the nuclear fuel rod with X-ray radiation to generate a series of angularly displaced images of the nuclear fuel rod via direct radiography, such that the circumference of the nuclear fuel pellets is substantially imaged;
inspecting the series of angularly displaced images to detect nuclear fuel pellet defects;
translating and/or rotating the nuclear fuel rod using a nuclear fuel rod positioning mechanism after producing the series of angularly displaced images;
irradiating the nuclear fuel rod with an additional portion of X-ray radiation to produce a second set of angularly displaced images;
dividing, using one or more algorithms executed by a processing circuit, each image of the set of angularly displaced images by the corresponding image of the second set to produce a digital representation of the quotient;
inspecting the digital representation for any areas comprising a value less than or greater than one;
wherein the nuclear fuel rod is translated between about 1 micron and about 1 centimeter, and/or the nuclear fuel rod is rotated less than about 3 degrees.

* * * * *